US00PP19506P2

(12) United States Plant Patent
Rijnbeek

(10) Patent No.: US PP19,506 P2
(45) Date of Patent: Nov. 25, 2008

(54) ***GERANIUM* PLANT NAMED 'MELINDA'**

(50) Latin Name: ***Geranium endressii*×*Geranium sylvaticum***
Varietal Denomination: Melinda

(76) Inventor: Anthonius Philippus Maria Rijnbeek, Reijerskoop 303, 2771 BL Boskoop (NL)

( * ) Notice: Subject to any disclaimer, the term of this patent is extended or adjusted under 35 U.S.C. 154(b) by 0 days.

(21) Appl. No.: 11/999,270

(22) Filed: Dec. 4, 2007

(51) Int. Cl.
*A01H 5/00* (2006.01)

(52) U.S. Cl. ..... Plt./324

(58) Field of Classification Search ..... Plt./324
See application file for complete search history.

*Primary Examiner*—Kent L. Bell
*Assistant Examiner*—Georgia Helmer
(74) *Attorney, Agent, or Firm*—C. A. Whealy

(57) ABSTRACT

A new and distinct cultivar of *Geranium* plant named 'Melinda', characterized by its upright plant habit; strong growth habit; freely branching habit; freely flowering habit; light pink-colored flowers with red purple-colored venation; and good garden performance.

2 Drawing Sheets

Botanical designation: *Geranium endressii*×*Geranium sylvaticum.*
Cultivar denomination: 'Melinda'.

BACKGROUND OF THE INVENTION

The present invention relates to a new and distinct cultivar of *Geranium,* botanically known as *Geranium endressii*× *Geranium sylvaticum,* and hereinafter referred to by the name 'Melinda'.

The new *Geranium* is a chance seedling from a cross-pollination made in the spring of 2000 of an unnamed selection of *Geranium endressii,* not patented, as the female, or seed, parent with the *Geranium sylvaticum* cultivar Mayflower, not patented as the male, or pollen, parent. The new *Geranium* was discovered and selected by the Inventor as a single flowering plant from within the progeny of the stated cross-pollination grown in a controlled environment in Boskoop, The Netherlands in the spring of 2004.

Asexual reproduction of the new *Geranium* by divisions in a controlled environment in Boskoop, The Netherlands since 2004, has shown that the unique features of this new *Geranium* are stable and reproduced true to type in successive generations.

SUMMARY OF THE INVENTION

The cultivar Melinda has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Melinda'. These characteristics in combination distinguish 'Melinda' as a new and distinct cultivar of *Geranium:*

1. Upright plant habit.
2. Strong growth habit.
3. Freely branching habit.
4. Freely flowering habit.
5. Light pink-colored flowers with red purple-colored venation.
6. Good garden performance.

Plants of the new *Geranium* differ primarily from plants of the female parent selection primarily in flower color as plants of the female parent selection have blue-colored petals.

Plants of the new *Geranium* differ primarily from plants of the male parent, the cultivar Mayflower, primarily in flower color as plants of the cultivar Mayflower have rose pink-colored flowers. In addition, plants of the new *Geranium* are larger and more upright than plants of the cultivar Mayflower.

Plants of the new *Geranium* can be compared to plants of the *Geranium sylvaticum* cultivar Meran, not patented. In side-by-side comparisons conducted in Boskoop, The Netherlands, plants of the new *Geranium* differed primarily from plants of the cultivar Meran in flower colors as plants of the cultivar Meran had blue lavender-colored flowers.

BRIEF DESCRIPTION OF THE PHOTOGRAPHS

The accompanying colored photographs illustrate the overall appearance of the new *Geranium,* showing the colors as true as it is reasonably possible to obtain in colored reproductions of this type. Colors in the photographs may differ slightly from the color values cited in the detailed botanical description which accurately describe the colors of the new *Geranium.*

The photograph on the first sheet comprises a side perspective view of a typical flowering plant of 'Melinda' grown in a container.

The photograph at the top of the second sheet is a close-up view of a typical leaf of 'Melinda'.

The photograph at the bottom of the second sheet is a close-up view of typical flowers of 'Melinda'.

DETAILED BOTANICAL DESCRIPTION

The aforementioned photographs and following observations, measurements and values describe plants grown in Boskoop, The Netherlands in an outdoor nursery during the spring. During the production of the plants, day temperatures ranged from 9° C. to 25° C. and night temperatures ranged from 2° C. to 12° C. Plants were about one year old when the photographs and the description were taken. In the detailed description, color references are made to The Royal Horticultural Society Colour Chart, 2001 Edition, except where general terms of ordinary dictionary significance are used.

Botanical classification: *Geranium endressii*×*Geranium sylvaticum* cultivar Melinda.

Parentage:

*Female, or seed, parent.*—Unnamed selection of *Geranium endressii*, not patented.

*Male or pollen parent.*—*Geranium sylvaticum* cultivar Mayflower, not patented.

Propagation:

*Type.*—By divisions.

*Time to produce a rooted young plant, summer.*—About 20 weeks.

*Root description.*—Medium thickness, moderately fleshy; N199A in color.

*Rooting habit.*—Moderately dense.

Plant description:

*General appearance.*—Herbaceous perennial. Upright plant habit.

*Growth and branching habit.*—Moderately vigorous to vigorous growth habit. Freely basal branching habit with about seven lateral branches developing per plant.

*Plant height, to top of umbels.*—About 32.7 cm.

*Plant width.*—About 20.6 cm.

*Lateral branches.*—Length: About 16.1 cm. Diameter: About 3 mm. Internode length: About 9.5 cm. Texture: Moderately pubescent. Strength: Moderately strong. Color: 144A.

Foliage description:

*Arrangement.*—Opposite, simple.

*Length.*—About 6.4 cm.

*Width.*—About 7.9 cm.

*Shape.*—Reniform; palmate.

*Apex.*—Acute.

*Base.*—Hastate.

*Margin.*—Palmately cleft; lobes biserrate.

*Venation pattern.*—Palmate.

*Texture, upper and lower surfaces.*—Moderately pubescent.

*Color.*—Developing foliage, upper surface: 143A. Developing foliage, lower surface: Between 143C and 144A. Fully developed, upper surface: 137B; venation, 144B. Fully developed, lower surface: 138B; venation, 138B.

*Petiole.*—Length: About 2.5 cm. Diameter: About 2.5 mm. Diameter: About 0.8 mm. Texture, upper and lower surfaces: Pubescent. Color, upper and lower surfaces: 144A.

Flower description:

*Flower arrangement.*—Single rotate flowers arranged in pairs arising from apical leaf axils. Flowers face mostly upright. Flowers not fragrant.

*Quantity of flowers.*—Freely flowering habit; about twelve flower buds and open flowers per lateral branch.

*Flowering season.*—In The Netherlands, flowering is continuous from spring to early autumn. Flowers not persistent.

*Flower longevity.*—Flowers last about one week on the plant.

*Flower diameter.*—About 3.1 cm.

*Flower depth* (*height*).—About 1.2 cm.

*Flower buds.*—Length: About 9 mm. Diameter: About 4.5 mm. Shape: Elliptic. Color: 138B; upper surface, 152B.

*Petals.*—Quantity per flower: Five in a single whorl. Length: About 1.8 cm. Width: About 1.4 cm. Shape: Obcordate. Apex: Obtuse. Base: Attenuate. Margin: Entire. Texture, upper and lower surfaces: Mostly smooth; towards the base, densely pubescent. Color: When opening, upper surface: Between 76C and N155A; venation, N74B. When opening, lower surface: Between 76C and N155A; venation, N74C. Fully opened, upper surface: N155A tinted with 76C; venation, N74C. Color becoming closer to between 76C and N155A and venation, N74D. Fully opened, lower surface: N155A tinted with 76C; venation, N74D.

*Sepals.*—Quantity per flower: Five, arranged in a single whorl. Length: About 1 cm. Width: About 4 mm. Shape: Ovate. Apex: Mucronate. Base: Cuneate. Margin: Entire. Texture, upper surface: Smooth, glabrous. Texture, lower surface: Pubescent. Color: When opening, upper and lower surfaces: Between 138B and 152B. Fully opened, upper and lower surfaces: 144B.

*Peduncles.*—Length: About 2.4 cm. Diameter: About 1.5 mm. Strength: Moderately strong. Angle: About 20° C. from vertical. Texture: Pubescent. Color: 144A to 144B; upper surface flushed with 176A to 176B.

*Pedicels.*—Length: About 1.3 cm. Diameter: About 1 mm. Strength: Moderately strong. Angle: About 20° C. from vertical. Texture: Pubescent. Color: 144A to 144B; upper surface flushed with 176A to 176B.

*Reproductive organs.*—Androecium: Stamen quantity per flower: About ten. Filament length: About 9 mm. Filament color: 65D; towards the base, N155B. Anther length: About 2 mm. Anther width: About 0.75 mm. Anther shape: Oblong. Anther color: 161D. Pollen amount: Moderate to abundant. Pollen color: 10B. Gynoecium: Pistil quantity per flower: One. Pistil length: About 7 mm. Stigma shape: Five-parted; reflexed. Stigma color: 180C. Style length: About 4 mm. Style color: 146C to 146D. Ovary color: 143B to 143C.

*Seed.*—Seed development has not been observed.

Disease/pest resistance: Plants of the new *Geranium* have not been observed to be resistant to pathogens and pests common to *Geraniums*.

Garden performance: Plants of the new *Geranium* have exhibited good garden performance and to tolerate rain and wind and have been observed to be suitable for USDA Zones 5 to 9.

It is claimed:

1. A new and distinct *Geranium* plant named 'Melinda' as illustrated and described.

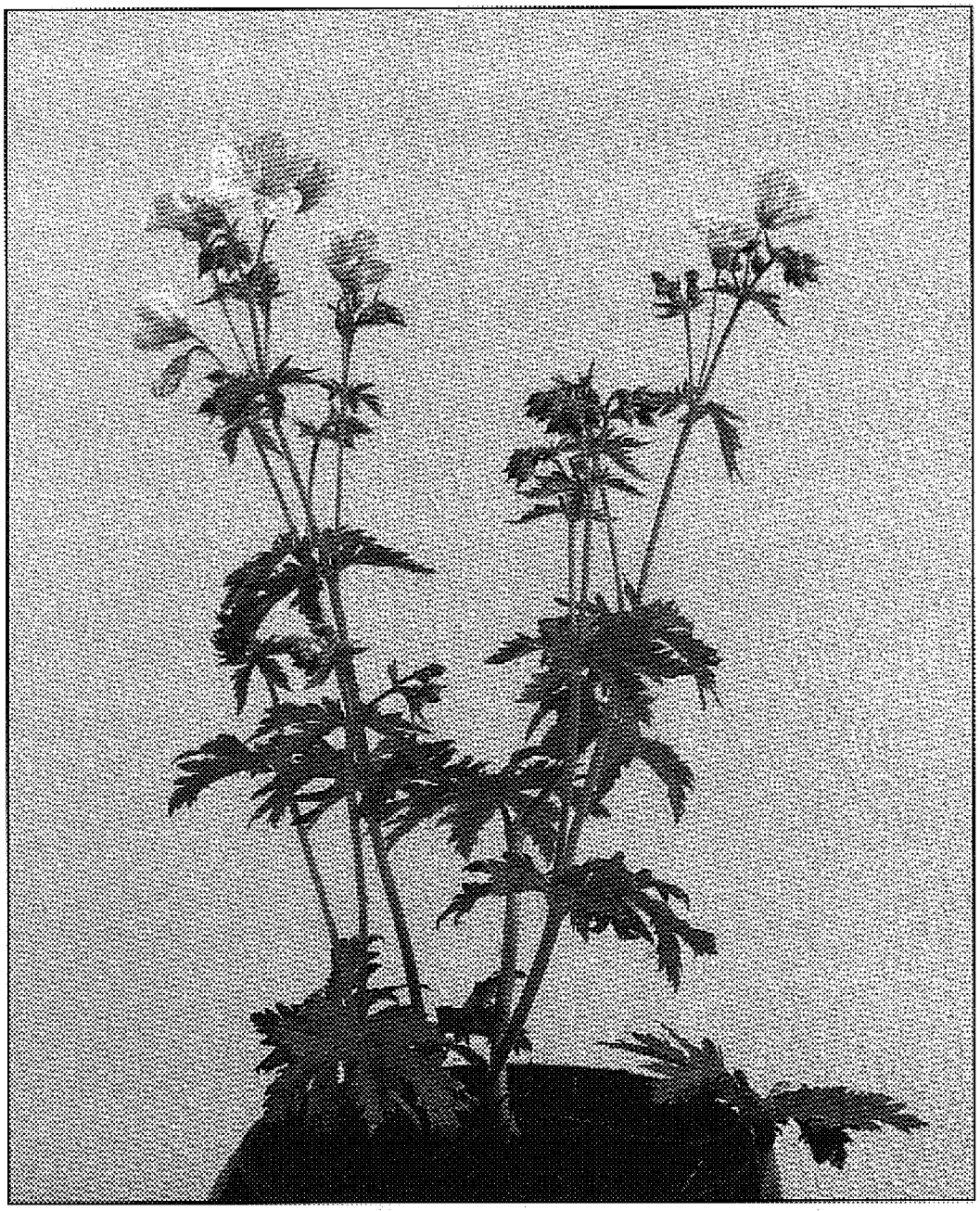

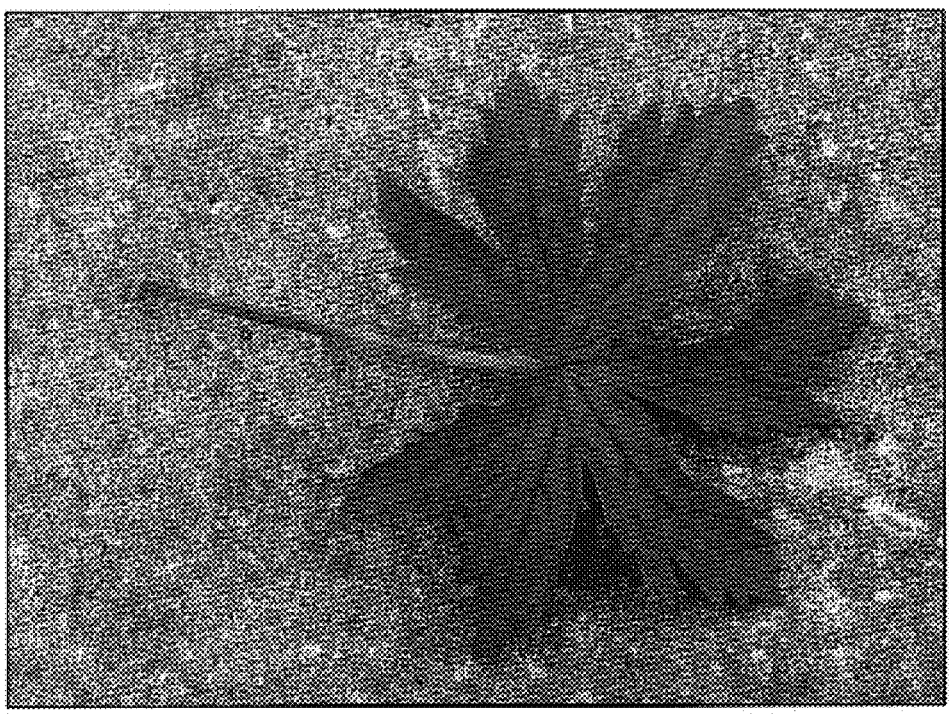
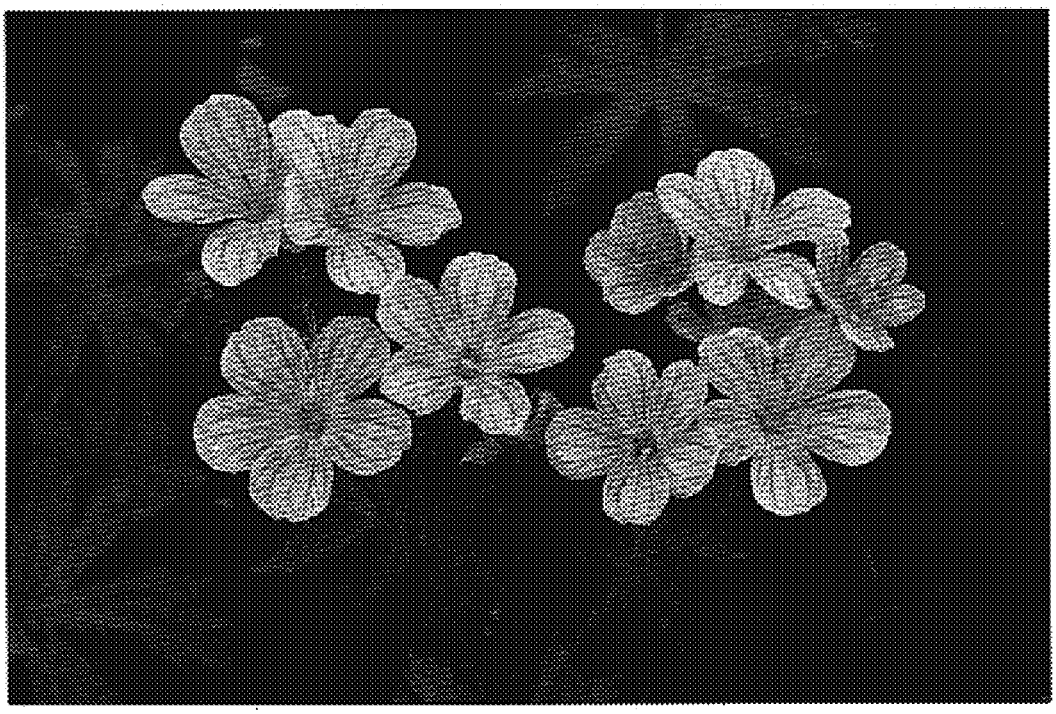

* * * * *